(12) United States Patent
Loganathan et al.

(10) Patent No.: US 11,642,656 B2
(45) Date of Patent: May 9, 2023

(54) CATALYST COMPOSITION FOR OXIDATIVE DEHYDROGENATION OF ALKANE

(71) Applicant: INDIAN OIL CORPORATION LIMITED, Maharashtra (IN)

(72) Inventors: Kumaresan Loganathan, Faridabad (IN); Arumugam Velayutham Karthikeyani, Faridabad (IN); Hima Bindu Doosa, Faridabad (IN); Ram Mohan Thakur, Faridabad (IN); Alex Cheru Pulikottil, Faridabad (IN); Madhusudan Sau, Faridabad (IN); Gurpreet Singh Kapur, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 201 days.

(21) Appl. No.: 17/140,922

(22) Filed: Jan. 4, 2021

(65) Prior Publication Data
US 2021/0205789 A1  Jul. 8, 2021

(30) Foreign Application Priority Data
Jan. 2, 2020  (IN) .............................. 202021000190

(51) Int. Cl.
| | |
|---|---|
| *B01J 21/08* | (2006.01) |
| *B01J 21/04* | (2006.01) |
| *B01J 21/12* | (2006.01) |
| *B01J 23/02* | (2006.01) |
| *B01J 23/04* | (2006.01) |
| *B01J 23/10* | (2006.01) |
| *B01J 23/22* | (2006.01) |
| *B01J 23/26* | (2006.01) |
| *B01J 27/25* | (2006.01) |
| *B01J 35/02* | (2006.01) |
| *B01J 35/08* | (2006.01) |
| *B01J 35/10* | (2006.01) |
| *B01J 37/00* | (2006.01) |
| *B01J 37/08* | (2006.01) |
| *C07C 5/48* | (2006.01) |

(52) U.S. Cl.
CPC .............. *B01J 21/08* (2013.01); *B01J 21/04* (2013.01); *B01J 21/12* (2013.01); *B01J 23/02* (2013.01); *B01J 23/04* (2013.01); *B01J 23/10* (2013.01); *B01J 23/22* (2013.01); *B01J 23/26* (2013.01); *B01J 27/25* (2013.01); *B01J 35/023* (2013.01); *B01J 35/08* (2013.01); *B01J 35/1014* (2013.01); *B01J 35/1019* (2013.01); *B01J 35/1038* (2013.01); *B01J 37/0018* (2013.01); *B01J 37/0072* (2013.01); *B01J 37/088* (2013.01); *C07C 5/48* (2013.01); *C07C 2521/04* (2013.01); *C07C 2521/08* (2013.01); *C07C 2521/12* (2013.01); *C07C 2523/02* (2013.01); *C07C 2523/04* (2013.01); *C07C 2523/10* (2013.01); *C07C 2523/22* (2013.01); *C07C 2523/26* (2013.01)

(58) Field of Classification Search
CPC ... B01J 21/08; B01J 21/04; B01J 21/12; B01J 23/02; B01J 23/04; B01J 23/10; B01J 23/22; B01J 23/26; B01J 27/25; B01J 35/023; B01J 35/08; B01J 35/1014; B01J 35/1019; B01J 35/1038; B01J 37/0018; B01J 37/0072; B01J 37/088; C07C 5/48; C07C 2521/04; C07C 2521/08; C07C 2521/12; C07C 2523/02; C07C 2523/04; C07C 2523/10; C07C 2523/22; C07C 2523/26
USPC ....... 502/201, 247, 248, 243, 250, 256, 303, 502/304, 312
See application file for complete search history.

(56) References Cited

U.S. PATENT DOCUMENTS

| | | | | |
|---|---|---|---|---|
| 3,542,671 A | * | 11/1970 | Pollitzer | .................. B01J 23/42 585/277 |
| 3,925,498 A | * | 12/1975 | Stadig | .................... B01J 8/0453 558/383 |
| 8,063,261 B2 | | 11/2011 | Rokicki et al. | |
| 8,101,541 B2 | | 1/2012 | Fridman | |
| 8,895,468 B2 | | 11/2014 | Ruettinger et al. | |
| 9,963,407 B2 | * | 5/2018 | Stine | ......................... C07C 5/48 |
| 2005/0075243 A1 | | 4/2005 | Fridman et al. | |
| 2016/0228851 A1 | * | 8/2016 | Hermans | .................. B01J 23/30 |
| 2018/0214852 A1 | | 8/2018 | Fridman | |

FOREIGN PATENT DOCUMENTS

| | | | | |
|---|---|---|---|---|
| CN | 1939588 | * | 4/2007 | .............. Y02P 20/52 |
| CN | 105817258 | * | 8/2016 | ........... C07C 5/3332 |
| RU | 2627667 C1 | | 8/2017 | |
| WO | WO 2007/086839 | * | 8/2007 | .............. B01J 8/082 |
| WO | 2014046659 A1 | | 3/2014 | |
| WO | WO-2018025117 A1 | * | 2/2018 | .............. B01J 35/00 |

OTHER PUBLICATIONS

Atanga et al. "Oxidative Dehydrogenation of Propane to Propylene with Carbon Dioxide" Applied Catalysis B: Environmental; May 2017.

* cited by examiner

*Primary Examiner* — Patricia L. Hailey
(74) *Attorney, Agent, or Firm* — Maschoff Brennan

(57) ABSTRACT

The present invention provides a catalyst composition for the production of olefins from lighter alkanes by oxidative dehydrogenation route and methods of making the dehydrogenation catalyst composites.

13 Claims, No Drawings

CATALYST COMPOSITION FOR OXIDATIVE DEHYDROGENATION OF ALKANE

FIELD OF THE INVENTION

The present invention relates to a catalyst composition for the production of olefins from lighter alkanes by oxidative dehydrogenation route and methods of making the dehydrogenation catalyst composites. In particular, this invention relates to a process for the preparation of dehydrogenation catalyst microsphere support by employing inorganic nitrate binder, high active silica/silica-alumina and hydrothermally stable alumina.

BACKGROUND OF THE INVENTION

Lighter olefins, such as ethylene, propylene and butylene, are produced by dehydrogenating corresponding lighter alkanes. Platinum supported on alumina catalysts, noble metal promoted zinc aluminate spinel catalysts, or chromium oxide supported alumina catalysts are industrially used for dehydrogenation of alkanes. However, these catalysts have two main drawbacks. First, it is difficult to obtain high olefin yields due to equilibrium limitations of the dehydrogenation reaction. Second, at high temperatures the catalysts deactivate rapidly.

Catalytic oxidative dehydrogenation (ODH) is an emerging technology, which can eliminate some of the drawbacks associated with the conventional cracking processes. Since oxidative dehydrogenation catalysts play an important role in such reactions, much ongoing research work focuses on different aspects of the catalysis process. These aspects include catalyst active phases, structure and morphology which are all responsible for the catalyst performance. Furthermore, in the area of oxidative dehydrogenation of alkane, catalyst selectivity can be one of the most important factors influencing performance, in addition to catalyst stability and other parameters.

One type of catalyst commonly used for dehydrogenating lower alkanes is an alumina supported chromium oxide catalyst. Although this catalyst has a relatively high dehydrogenation activity, it may suffer from rapid coke formation during the dehydrogenation reaction. Consequently, frequent high temperature regeneration cycles are required. Due to the need for frequent regeneration, it is desired to have a high degree of hydrothermal stability for the catalyst in order to prevent catalyst loss and catalyst replacement. Regeneration is performed with pre-heated air through a direct fire burner or with the exhaust of a gas turbine. Regeneration temperatures range from 550-750° C. As a result of such severe operating conditions, dehydrogenation catalyst life is typically one to less than two years. Catalyst replacement is performed when conversion and selectivity fall below minimum levels required for the economic operation of the unit.

Few studies are available in literature which attempts to address one or more of these issues. However, they do not completely address all the above-mentioned pertinent issues.

US20050075243A1, U.S. Pat. No. 8,063,261B2 and U.S. Pat. No. 8,101,541B2 by Sued Chemie Inc., disclose a stationary or fluid bed dehydrogenation catalyst containing an alumina carrier, with chromium for hydrocarbons, which is particularly useful in vapor phase dehydrogenation.

U.S. Pat. No. 8,895,468B2 by SABIC Global Technologies BV, and WO2014046659A1 by BASF SE, relates to the preparation of a dehydrogenation catalyst comprising $Cr_2O_3$, an alkali metal oxide, $SiO_2$ and $Al_2O_3$, and methods of using said catalyst to make an olefin and/or dehydrogenate a dehydrogenatable hydrocarbon. Oxidative dehydrogenation of propane to propylene with carbon dioxide was reviewed by Atanga et al. (*Appl Catal B.* 220 (2018) 429-445) and various catalyst system such as CrO on alumina/zirconia/silica/titania/magnium oxide in presence of $CO_2$ is discussed.

RU2627667C1 by National Research Tomsk State University relates to a nano-structured catalyst synthesized by impregnating zirconium oxide with an aqueous solution containing $CrO_3$ and the soluble salts of potassium and/or sodium for the dehydrogenation of $C_3$-$C_5$ paraffins.

US20180214852A1 by Clariant Corp., relates to methods for making chromium-containing dehydrogenation catalysts using chromium feedstocks that need not include chromium (VI).

SUMMARY OF THE INVENTION

Catalytic oxidative dehydrogenation shows promise as a strategy for the production of olefins from lighter alkanes. It overcomes the drawbacks like low olefin yields due to equilibrium limitations of the dehydrogenation reaction and rapid deactivation of the catalyst at high temperatures. Therefore, oxidative dehydrogenation catalysts play an important role in reactions and there is lot of ongoing research work focusing on different aspects of the catalysis process.

Advantages of the Invention

The following are the technical advantages of the present invention over the aforementioned prior arts:
Superior hydrothermal stability,
High apparent bulk density (ABD) (0.75-0.95 g/cc),
Low attrition index,
High alkane conversion (above 50%) and
High olefin selectivity (above 70%).

OBJECTIVES OF THE PRESENT INVENTION

It is the main objective of the present invention to provide a catalyst composition for the production of olefins from lighter alkanes by oxidative dehydrogenation route and methods of making the dehydrogenation catalyst composites.

Further the object of this invention is to provide a process for the preparation of dehydrogenation catalyst microsphere support by employing inorganic nitrate binder, high active silica/silica-alumina and hydrothermally stable alumina.

Further the object of the invention is to provide a process for the preparation of dehydrogenation catalyst microsphere support in which an element of the rare earth group is used for doping the alumina to obtain hydrothermal stability.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such components of the composition, steps of the process, features of the composition, referred to or indicated in this specification, individually or collectively, and any and all combinations of any or more of such components or steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally equivalent products and processes are clearly within the scope of the disclosure, as described herein.

Selective dehydrogenation of propane to propylene is one of the major challenges for production of valuable and versatile chemical feedstocks. The current industrial on-purpose propylene production through dehydrogenation of ethane and propane is non-oxidative in nature and is contributing to quick catalyst deactivation, low conversion and selectivity, and high reaction temperatures. The current state-of-the-art research has primarily focused on investigating the synergistic effects between gas phase oxidants and alkanes in order to overcome the hindrances in current industrial dehydrogenation reactions. Oxidative dehydrogenation of propane (OPDH) in the presence of molecular $O_2$, as an oxidizing agent, favors low temperature reactions and is exothermic with no thermodynamic limitations, deep oxidation of propane and propylene to $CO_2$ is a major drawback, which often results in lowering the propylene selectivity and yield. To address these issues, an alternative approach has been proposed by which $O_2$ is replaced with a milder oxidant such as $CO_2$ to convert propane to propylene over various heterogeneous catalysts.

With the expected high future demand for propylene, commercialization of oxidative dehydrogenation reactions that uses $CO_2$ will not only meet the demand for propylene, it may also create a way to combat climate change. Therefore, an effective catalyst for OPDH should have affinity for both $CO_2$ and C—H over C—C bond cleavage to avoid side reactions. Moreover, as $CO_2$ is slightly acidic, it would preferentially adsorb onto the basic sites of the catalyst, while propane and $H_2$ would adsorb on the acidic sites. Therefore, a balance of acidity and basicity is required to avoid unwanted side and secondary reactions including propane hydrogenolysis, thermolytic and catalytic cracking, and isomerization reaction.

The present invention provides a catalyst composition for the production of olefins from lighter alkanes by oxidative dehydrogenation. This catalyst composition provides superior hydrothermal stability, high ABD (0.75-0.95 g/cc), low attrition index, high alkane conversion (above 50%) and high olefin selectivity (above 70%).

In an embodiment of the invention, the catalyst composition for the production of olefins from lighter alkanes by oxidative dehydrogenation comprises microsphere catalyst support material, catalytic material, and promoter. The microsphere catalyst support material comprises binder, high surface area silica/silica-alumina and hydrothermally stable alumina.

In an embodiment of the invention, the binder in the microsphere catalyst material comprises inorganic nitrate binder.

In an embodiment of the invention, the inorganic nitrate binder is present in an amount ranging from 1-10% in the form of a solution.

In another embodiment, the high surface area silica/silica-alumina in the microsphere catalyst support material is selected from a group consisting of fumed silica, spray dried silica from ammonium polysilicate, amorphous silica-alumina, MCM-41 (Mobil Composition of Matter No. 41), SBA-15 (Santa Barbara Amorphous-15), SAPO-11 (silicoa-luminophosphate-11), and combinations thereof.

In one feature, the alumina in the microsphere catalyst support material is modified with an f-block element to obtain hydrothermal stability. In this, the f-block element is selected from a group consisting of lanthanum and cerium.

In yet another feature, the lanthanum or cerium is present at a concentration of 0.1 wt % to 5 wt %, based on the total weight of the catalyst.

In an embodiment, the catalytic material comprises a vanadium-chromium complex 30 disposed on the microsphere catalyst support material. Additionally, vanadium oxide is present at a concentration of 0.1 wt % to 20 wt %, based on the total weight of the catalyst. Similarly, chromium oxide is present at a concentration of 0.5 wt % to 25 wt %, based on the total weight of the catalyst.

In another embodiment, the promoter in the microsphere catalyst support material comprises an alkali metal oxide or an alkaline oxide. The alkali metal oxide is selected from a group consisting of sodium, potassium, rubidium, cesium, and combinations thereof. The alkaline oxide is selected from a group consisting of beryllium, magnesium, calcium, strontium, barium, and combinations thereof. The alkali or alkaline oxide is present in an amount ranging from 0.1 wt % to 2 wt %, based on the total weight of the catalyst.

In yet another embodiment, a process for preparation of a dehydrogenation catalyst comprises the steps of preparing an f-block element modified alumina; preparing a binder; preparing a microsphere catalyst support using the f-block element modified alumina, the binder and a high surface area silica/silica-alumina; impregnating a vanadium-chromium complex on the microsphere catalyst support; and impregnating a promoter on the microsphere catalyst support.

In another aspect, the present invention provides a process for preparing of dehydrogenation catalyst for alkane. The process comprises:
  (a) reacting nitric acid, lanthanum/cerium nitrate with sodium aluminate at a temperature of about 80 to about 130° C. to obtain a slurry, continuing the reaction until pH of the slurry is reached to about 9.5, hydrothermal treatment of wet cake at a crystallization temperature of about 70 to about 130° C. for the duration of 10-48 h and filter the crystallize material to obtain hydrothermally stable pseudoboehmite alumina support;
  (b) reacting aluminium nitrate with water at temperature of about 70° C. to obtain clear viscous binder solution;
  (c) reacting binder solution with high surface area silica/silica-alumina and hydrothermally stable alumina under stirring at temperature of about 30° C. to obtain slurry with solid content of 15-25% for spray drying;
  (d) spray drying the slurry of step (c) to obtain microspheres of pseudoboehmite alumina support;
  (e) calcining the microspheres of step (d) at a temperature of about 650° C. for the duration of 3-5 h to obtain calcined microspheres;
  (f) impregnating the microspheres of step (e) with vanadium-chromium based complex, drying and calcining at a temperature of about 650° C. for the duration of 3-5 hours; and
  (g) impregnating the calcined catalyst of step (f) with promoters metal ions drying and calcining at a temperature of about 600° C. for the duration of 3-5 hours.

In an embodiment of the invention, the solid content of the slurry in step (c) is from 15% to 25%.

In another embodiment of the invention, vanadium oxide and chromium oxides are considered to be the most important and useful metals to be used as a catalyst due to their physical and chemical properties. The catalytic activity of vanadium oxide/chromium oxide are attributed to their reducible nature and ability to easily change their oxidation state ($V^{3+}$ to $V^{5+}$/$Cr^{3+}$ to $Cr^{6}$) $V^{5+}$ and $Cr^{3+}$ are the highly active initial state of the catalyst for oxidative dehydrogenation.

EXAMPLES

Having described the basic aspects of the present invention, the following non-limiting example illustrates the specific embodiments thereof. Those skilled in the art will appreciate that many modifications may be made in the invention without changing the essence of invention.

Example 1

Step 1: Preparation of 2 wt % RE (Rare Earth Elements) Doped Alumina

In the first step, 401 grams of concentrated nitric acid ($HNO_3$) along with appropriate amount of nitrate of rare earth elements was added to 2571 grams of demineralized water (DM) water and this acidic solution was denoted as Solution A. Solution A was heated to 80° C. in water bath and 780 grams of sodium aluminate solution (20% $Al_2O_3$, 30% $Na_2O$ and 50% water) was added into solution A. Further, the reaction mixture was crystallized at 80° C.-130° C. in an autoclave for one day. Then the alumina prepared was withdrawn from the autoclave and washed with hot DM water for 5-6 times to eliminate impurities from the material. The cake obtained from this process after washing was dried and then calcined at 550° C. for 2 hours.

The alumina prepared in Step 1 above was tested for its hydrothermal stability in auto steaming unit. 50 grams of alumina was loaded into a reactor. The reactor was heated at a temperature of about 700° C. under contact flow of nitrogen gas. After reaching a temperature of about 700° C., it was heated for 1 hour. After 1 hour, steam was supplied for 4 ml/hour for 3 hours at a temperature of about 700° C. The reactor was cooled down to room temperature of about 25-30° C. The downloaded alumina was characterized for surface area and pore size distribution under $N_2$ sorption analysis method.

TABLE 1

Physico-chemical properties of RE stabilized alumina

| Sr. No | Description of alumina | Surface area ($m^2g^{-1}$) | Total pore volume ($m^3g^{-1}$) | BJH Desorption % | | |
|---|---|---|---|---|---|---|
| | | | | >120 Å | 60-120 Å | <60 Å |
| 1 | Alumina with 2 wt % of $La_2O_3$ | 190 | 0.42 | 14.2 | 47.6 | 38.3 |
| 2 | Alumina (HTD) with 2 wt % of $La_2O_3$ | 144 | 0.40 | 65.8 | 32.1 | 2.2 |
| 3. | Alumina with 2 wt % of $CeO_2$ | 204 | 0.42 | 10.5 | 40.4 | 49.1 |
| 4. | Alumina (HTD) with 2 wt % of $CeO_2$ | 119 | 0.42 | 50.3 | 48.8 | 0.9 |
| 5. | Alumina without rare earth | 218 | 0.40 | 13.3 | 52.7 | 33.9 |
| 6. | Alumina without rare earth (HTD) | 85 | 0.36 | 39.2 | 50.1 | 10.7 |

*HTD Hydrothermally deactivated

Step 2: Preparation of High Surface Area Silica/Silica-Alumina

MCM-41 (Mobil Composition of Matter No. 41), SBA-15 (Santa Barbara Amorphous-15), fumed silica, spray dried silica from ammonium poly silicate, SAPO-11 (silicoaluminophosphate-11), amorphous silica-alumina synthesized/obtained commercially was used in the catalyst preparation as support.

Step 3: Preparation of Binder

Pseudoboehmite alumina having high binding property was mixed with 1-10 wt % aluminum nitrate solution to obtain peptized gel, used to bind matrix and active alumina/silica support.

Step 4: Preparation of Microsphere (20-150μ) Catalyst Support

Rare Earth (RE) doped alumina (110 grams), active high surface area silica/silica-alumina from Step 2 (275 grams) was mixed with DM water (400 grams) and the slurry was milled in an attritor/wet ball mill for 30 minutes. Then, 510 grams of binder gel prepared from Step 3 was mixed with the milled slurry. The final slurry was stirred for 30 minutes to obtain homogenized slurry with solid content of 20-22 wt %. This slurry was spray dried to produce green catalyst support microspheres. The catalyst support microsphere (20-150μ particle size range) was calcined at 650° C. for 4 hours.

Step 5: Impregnation of Metal (Cr, V) on Catalyst Microsphere Support

Calcined catalyst microsphere (100 grams) with particle size range of 20-150μ was used as support for catalyst preparation. Ammonium metavanadate was dissolved in monoethanolamine to obtain yellow color clear solution. Ammonium dichromate was dissolved in DM water and then added into ammonium metavanadate-monoethanolamine solution to form a dark green Cr—V complex. The dark green solution wan then used to impregnate to form catalyst on the microsphere catalyst support. The impregnated wet catalyst was dried at 120° C. for 10 hours and calcined at 600° C. for 2 hours.

Step 6: Impregnation of Promoter on Catalyst Microsphere 2.656 grams potassium nitrate was dissolved in 40 grams of DM water. This solution was added to 99 grams catalyst microspheres to impregnate potassium on catalyst microsphere. The impregnated wet catalyst was dried at 120° C. for 10 hours and calcined at 600° C. for 2 hours.

Results

Table 1 discloses the physico-chemical characterization and evaluation results of the oxidative dehydrogenation of propane catalyst.

TABLE 1

Results of OPDH Catalyst

| Sr. No. | Characteristics | Unit | Results |
|---|---|---|---|
| 1. | Surface area | $m^2/g$ | 216 |
| 2. | Pore volume | $m^3/g$ | 0.48 |
| 3. | Total acidity by ammonia TPD | mmol/g | 0.321 |
| 4. | Total hydrogen uptake by TPR | mmol/g | 5.8 |
| 5. | Apparent bulk density (ABD) | g/cc | 0.85 |
| 6. | Average particle size (APS) | μ | 82 |
| 7. | Attrition Index (ASTM D5757) | % | 2.1 |
| 8. | Propane conversion | % | 48 |
| 9. | Propylene selectivity | % | 89 |

It is concluded that the physico-chemical characterization and evaluation results of the oxidative dehydrogenation of propane catalyst shows propane conversion of 48% and propylene selectivity of 89%.

The invention claimed is:

1. A catalyst composition for production of olefins from lighter alkanes by oxidative dehydrogenation, wherein the catalyst composition comprises:
    a) a microsphere catalyst support material, wherein the microsphere catalyst support material comprises a binder, a high surface area silica/silica-alumina and a hydrothermally stable alumina;
    b) a catalytic material, wherein the catalytic material comprises a vanadium-chromium complex disposed on the microsphere catalyst support material, wherein the vanadium-chromium complex comprises vanadium oxide and chromium oxide; and
    c) a promoter.

2. The catalyst composition as claimed in claim 1, wherein the binder comprises an inorganic nitrate binder in the form of a solution present in an amount ranging from 1-10%.

3. The catalyst composition as claimed in claim 1, wherein the high surface area silica/silica-alumina is selected from the group consisting of fumed silica, spray dried silica from ammonium polysilicate, amorphous silica-alumina, and combinations thereof.

4. The catalyst composition as claimed in claim 1, wherein the alumina is modified with an f-block element to obtain hydrothermal stability; and wherein the f-block element is selected from the group consisting of lanthanum, cerium, and combinations thereof.

5. The catalyst composition as claimed in claim 4, wherein lanthanum or cerium is present at a concentration of 0.1 wt % to 5 wt %, based on the total weight of the catalyst.

6. The catalyst composition as claimed in claim 1, wherein vanadium oxide is present at a concentration of 0.1 wt % to 20 wt %, based on the total weight of the catalyst.

7. The catalyst composition as claimed in claim 1, wherein chromium oxide is present at a concentration of 0.5 wt % to 25 wt %, based on the total weight of the catalyst.

8. The catalyst composition as claimed in claim 1, wherein the promoter comprises an alkali metal oxide or an alkaline oxide; and wherein the alkali metal oxide or the alkaline oxide is present in an amount ranging from 0.1 wt % to 2 wt % based on the total weight of the catalyst.

9. The catalyst composition as claimed in claim 8, wherein the alkali metal oxide is selected from the group consisting of sodium, potassium, rubidium, cesium, and combinations thereof.

10. The catalyst composition as claimed in claim 8, wherein the alkaline oxide is selected from the group consisting of beryllium, magnesium, calcium, strontium, barium, and combinations thereof.

11. A process for preparation of a dehydrogenation catalyst, the process comprising:
    a) modifying hydrothermally stable alumina with an f block element;
    b) reacting an inorganic nitrate binder with water at a temperature of 70° C. to obtain a clear viscous binder solution;
    c) reacting the binder solution with a high surface area silica/silica-alumina and the hydrothermally stable alumina under stirring at a temperature of 30° C. to obtain a slurry with a solid content;
    d) spray drying the slurry of step (c) to obtain a microsphere catalyst support material;
    e) calcining the microsphere catalyst support material of step (d) at a temperature of 650° C. for a duration of 3-5 hours to obtain a calcined microsphere catalyst support material;
    f) impregnating the calcined microsphere catalyst support material of step (e) with a vanadium-chromium complex, drying and calcining at a temperature of 650° C. for a duration of 3-5 hours, wherein the vanadium-chromium complex comprises vanadium oxide and chromium oxide; and
    g) impregnating the calcined microsphere catalyst support material of step (f) with a promoter, drying and calcining at a temperature of 600° C. for a duration of 3-5 hours.

12. The process as claimed in claim 11, wherein the solid content of the slurry in step (c) is from 15 wt % to 25 wt %.

13. The process as claimed in claim 11, wherein the microsphere catalyst support material has a particle size in a range from 20μ to 150μ.

* * * * *